United States Patent [19]
Lidsky

[11] Patent Number: 5,602,150
[45] Date of Patent: Feb. 11, 1997

[54] TREATMENT OF CENTRAL NERVOUS SYSTEM DISORDERS ASSOCIATED WITH PSYCHOTIC BEHAVIOR AND DEMENTIA WITH A COMBINATION OF NEUROLEPTIC DRUGS AND TAURINE, OR DERIVATIVES THEREOF, TO PREVENT THE DEVELOPMENT OF TARDIVE DYSKINESIA

[75] Inventor: Theodore I. Lidsky, Atlantic Highlands, N.J.

[73] Assignee: Research Foundation for Mental Hygiene, Inc., Albany, N.Y.

[21] Appl. No.: 440,824

[22] Filed: May 15, 1995

Related U.S. Application Data

[63] Continuation of Ser. No. 956,109, Oct. 2, 1992, abandoned.
[51] Int. Cl.⁶ ........................ A61K 31/445; A61K 31/56; A61K 31/195; A61K 31/13
[52] U.S. Cl. ........................ 514/327; 514/171; 514/561; 514/565; 514/665
[58] Field of Search ........................ 514/410, 327, 514/665, 561, 565, 171

[56] References Cited

U.S. PATENT DOCUMENTS 4,271,189  6/1981  Durlach .................... 260/513

OTHER PUBLICATIONS

The Merck Manual, 14th ed., published by Merck & Co., Inc., pp. 2334–2337. 1982.

Primary Examiner—Raymond Henley, III
Attorney, Agent, or Firm— Morgan & Finnegan, LLP

[57] ABSTRACT

The present invention relates to a method of treatment and a composition used to prevent the development of the adverse manifestation of tardive dyskinesia in individuals suffering from mental illness such as schizophrenia and undergoing treatment with neuroleptic or antipsychotic agents. The experimentally-based rationale for the present invention indicates that conventional neuroleptic drugs induce tardive dyskinesia because they evoke a glutamate afflux whose excitotoxic action is unopposed by other properties of these drugs, including dopamine receptor blockade. The present invention provides effective drug therapies for schizophrenia comprising conventional neuroleptics or antipsychotic drugs given in combination with taurine, a taurine precursor such as hypotaurine, taurine derivatives, or compounds similar in action to taurine, to render benign tardive dyskinesia as an adverse effect. The combined administration of any of the conventional neuroleptics with taurine and the like offers the benefits of a safe and effective treatment that is generally affordable and vastly improves upon the limited, existing drug treatments which frequently exert crippling and long-lasting side effects unless drug is withdrawn.

34 Claims, 6 Drawing Sheets

DOPAMINE BASAL LEVEL

ACUTE COCAINE

HALDOL ADMINISTRATION

FIG. 4A
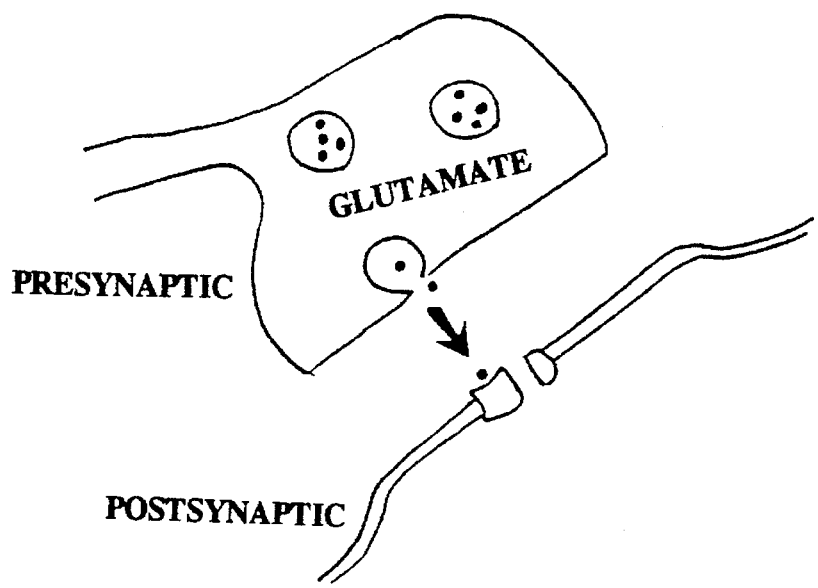
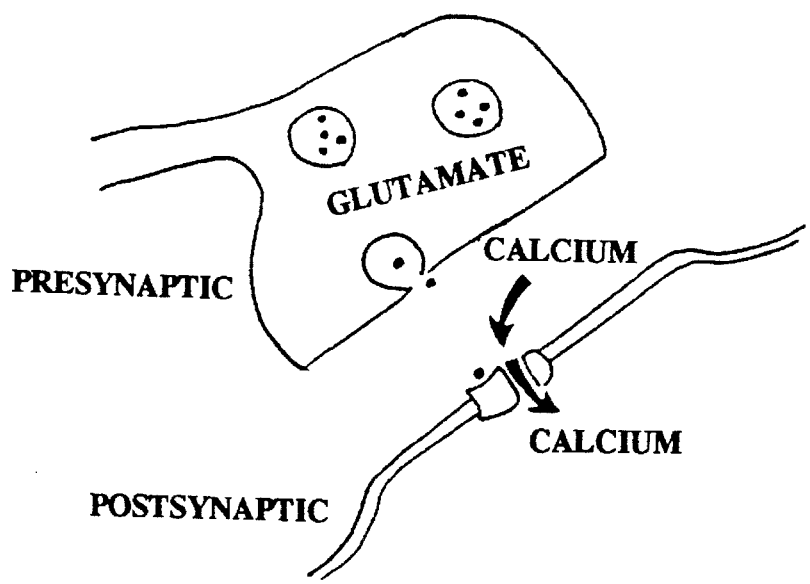
FIG. 4B

TREATMENT OF CENTRAL NERVOUS SYSTEM DISORDERS ASSOCIATED WITH PSYCHOTIC BEHAVIOR AND DEMENTIA WITH A COMBINATION OF NEUROLEPTIC DRUGS AND TAURINE, OR DERIVATIVES THEREOF, TO PREVENT THE DEVELOPMENT OF TARDIVE DYSKINESIA

This is a continuation of application Ser. No. 07/956,109 filed on Oct. 2, 1992 now abandoned.

FIELD OF THE INVENTION

The present invention relates generally to improvements in and preferred alternatives to treatments for mental illness, particularly schizophrenia, using neuroleptic agents in combination with taurine, its precursor, or similar molecules. Neuroleptic agents administered in conjunction with taurine lead to reduced risk for the development of the debilitating adverse side effect, tardive dyskinesia (TD), which is commonly observed following the use of other known treatments for mental illnesses.

BACKGROUND OF THE INVENTION

Schizophrenia was first characterized as a mental illness at the end of the nineteenth century. When the disease was initially described, it was noted that the general deterioration associated with this disease was inexorable. The variety of social, psychological, chemical, and surgical treatments and procedures tried for controlling schizophrenia at the end of the nineteen century were without positive effect.

In 1953, the introduction of neuroleptic drugs, such as chlorpromazine, into clinical practice, drastically changed the deplorable pre-existing situation concerning treatment for schizophrenia. The almost immediate ameliorative effects of these drugs heralded the new age of pharmacotherapy in psychiatry.

Neuroleptic agents or drugs (i.e. "neuroleptics"), also called anti-psychotics or major tranquilizers, remain the treatment of choice for schizophrenia, certain organic central nervous system disorders, mental illnesses, and associated psychotic processes today. Currently, it is estimated that over 95% of schizophrenics are chronically maintained on neuroleptics having pharmacological actions similar to the action of chlorpromazine, an aliphatic phenothiazine derivative which is also known generically as Thorazine.

Although the known anti-psychotic drugs have clear efficacy in the treatment of mental illness, they also have a variety of neurological side effects. The most clinically significant side effects are a host of movement disorders that are categorized based on extrapyramidal signs (EPS). Extrapyramidal signs include diverse symptoms such as Parkinsonism, akathesia, dystonia, torticollis, and oculogyric crisis. While these symptoms typically dissipate if drugs are withdrawn, psychotic relapse almost always occurs after the cessation of drug treatment. However, it has been found that pharmacological treatment with anti-cholinergic drugs is effective in treating EPS. Thus, the addition of anti-cholinergic agents such as cogentin or artane allows anti-psychotic medications to be maintained while many EPS are effectively treated.

Unfortunately, one type of EPS, a clinical manifestation called tardive dyskinesia (TD), is not amenable to any of the above-mentioned treatments. Through the years, it has become increasingly clear that a significant minority of the patients using neuroleptic drugs gradually develop TD which is a disfiguring movement disorder. Recent epidemiological studies have indicated serious rates of incidence of TD. For example, it is a conservative estimate that about 20% of all patients receiving anti-psychotic drugs and up to 70% of at-risk patients (e.g. elderly females) develop TD. The symptoms of TD most typically include involuntary movements of the facial and buccoloingual muscles. In some cases, the limbs, trunk, and even the respiratory apparatus can be affected. TD, unlike other EPS, is unresponsive to known pharmacological treatments. In addition, the severity of the symptoms of TD does not diminish with time. Indeed, the anti-cholinergic drugs which are used to alleviate other EPS syndromes actually increase the probability of inducing TD in patients treated with these drugs.

Because of its high incidence and irreversible nature, TD poses the most serious obstacle to successful pharmacotherapy for schizophrenia and some other organic central nervous system (CNS) disorders. The majority of cases of TD have been reported in patients with chronic schizophrenia, prolonged or repeated affective illness, or a variety of dementias. Importantly, however, TD also occurs in non-psychotic patients treated with neuroleptic agents for psychoneurosis, gastrointestinal disturbances, chronic pain syndromes, and personality disorders. As a consequence, strenuous efforts have been made to develop anti-psychotic drugs which do not produce TD.

To date, only one drug, clozapine, by itself possesses anti-psychotic potency and does not appear to cause TD. Unfortunately, clozapine carries a liability which has potentially more serious consequences to patients than any of the side effects associated with other conventional neuroleptics used for schizophrenia therapy. In a significant minority (e.g. at least about 2%) of all patients, clozapine leads to the development of agranulocytosis, a potentially fatal blood dyscrasia. The problem of agranulocytosis was deemed to be significant enough that, in spite of its advantages over other antipsychotic drugs, clozapine was pulled off the market after its initial introduction in Europe in the 1970's. Since the re-introduction of clozapine, weekly monitoring of blood levels is now necessary to insure the early detection of agranulocytosis. As a result of the required and continual monitoring process, the cost of clozapine treatment is prohibitive—about $6,000.00 to $9,000.00 per year per patient. This exceedingly high cost puts clozapine treatment far beyond the reach of most patients. Moreover, once a patient develops agranulocytosis from clozapine treatment, the reinstitution of therapy with this drug in surviving patients at a later time is absolutely precluded because of the almost certain recurrence of blood dyscrasia and its harmful effects. Thus, clozapine, which might be considered to be the drug of choice for treating schizophrenia, is actually a last resort.

Pathophysiological Basis of Tardive Dyskinesia (TD)

In view of the pharmacological actions of conventional neuroleptic drugs, the antipsychotic effects of these drugs have been generally correlated with their ability to block $D_2$ dopamine receptors. Dopamine has been recognized as a neurotransmitter in the central nervous system since 1959. Five important dopaminergic systems or pathways are now recognized in the brain. The first pathway, which is most closely related to behavior, is the mesolimbic-mesocortical pathway that projects from cell bodies near the substantia nigra to the limbic system and neocortex. The second pathway, the nigrostriatal pathway, consists of neurons that project from the substantia nigra to the caudate and putamen and is involved in voluntary movement coordination. The third pathway, the tuberoinfundibular system, connects arcuate nuclei and periventricular neurons (i.e. "nerve cells") to the hypothalamus and posterior pituitary. The fourth dopaminergic system, the medullary-periventricular pathway, consists of neurons in the motor nucleus of the vagus whose projections are not well-defined. The fifth pathway, the incertohypothalamic pathway, forms connections within the hypothalamus and to the lateral septal nuclei. The functions of this pathway are yet defined. In the early 1960's, evidence indicated that anti-psychotic drugs were dopamine antagonists, since these drugs were able to block the effects of dopamine on electrical activity in the central synapses and on the production of cyclic AMP by adenylate cyclase.

One theory put forth to explain the etiology of TD is the denervation supersensitivity of dopamine receptors following blockade of $D_2$ dopamine receptors. Although both $D_1$ and $D_2$ dopamine receptors exist, $D_2$ receptors are blocked by anti-psychotic agents in a stereospecific manner. $D_2$ receptors, in particular, proliferate after chronic treatment with antipsychotic drugs. Consideration of the differences in incidence and time course of TD reveals the weakness of the theory of dopamine receptor blockade as the sole cause of TD. For example, while all patients develop dopaminergic receptor supersensitivity within the first several weeks after neuroleptic use, only a minority of patients develop TD. The development of TD occurs over a period of several months to years of chronic medication. However, it should be noted that dopamine receptor sensitivity is probably a necessary first step in the cascade of neural changes brought about by chronic neuroleptic treatment that eventually culminates in TD. Thus, dopamine receptor sensitivity is necessary but not sufficient for TD development. It is noteworthy that, among the antipsychotic drugs, only Clozapine does not cause an increase in $D_2$ receptors.

The majority of $D_2$ dopamine receptors are located on dopamine-releasing neurons and act as inhibitory autoreceptors. As a result, the initial actions of neuroleptics should be to increase the action of dopamine by blocking autoreceptor-mediated negative feedback control of neurotransmitter synthesis and release. For example, microdialysis has revealed that neuroleptic drugs initially cause the release of dopamine from neurons (see FIGS. 1A,B,C). In addition, electrophysiological work of the inventor (FIG. 1D) has indicated that the initial postsynaptic blocking effects of neuroleptics are minimal (FIG. 1A). The inhibitory actions of dopamine on postsynaptic target cells are not blocked when dopamine release is mediated by the administration of neuroleptic drugs. Current work shows that the critical initiating event in the development of TD is the initial afflux of dopamine from dopamine-releasing nerve cells.

The pharmacologically-induced release of dopamine or the enhancement of its actions can have neurotoxic effects. Administration of the antipsychotic drug, haloperidol, also known as haldol, (described in U.S. Pat. No. 3,438,991, issued Apr. 15, 1969 to P. A. JanJanssen) also enhances dopamine release by blocking autoreceptors. In addition, electron micrographic studies have demonstrated evidence of neuronal degeneration in association with decreases in striatal dopamine levels. Haloperidol causes side effects, including acute EPS, after long-term administration. Dopamine can damage nerve cells by several different mechanisms. L-DOPA, the precursor of dopamine, and its hydroxylated derivatives are directly, albeit weakly, excitotoxic for neurons. Similarly, it has been suggested that oxidation products of dopamine may destroy neurons. Moreover, dopamine both potentiates the release of glutamate and also enhances its postsynaptic actions (Reid, M. S., Herrera-Marschitz, M., Kehr, J. and Ungerstedt, U. Striatal dopamine and glutamate release: Effects of intranigral injection of substance P. *Acta Physiol. Scand.*, 140: 527–537 (1990); Knapp, A. G., Schmidt, K. F. & Dowling, J. E. Dopamine modulates the kinetics of ion channels gated by excitatory amino acids in retinal ganglion cells. *Proc. Natl. Acad. Sci., USA*, 87: 767–771 (1990); Knapp, A. G. & Dowling, J. E. Dopamine enhances excitatory amino acid-gated conductances in cultured retinal horizontal cells. *Nature*, 325: 437–439 (1987)).

Excessive glutamatergic transmission is strongly excitotoxic and kills nerve cells. In principle, administration of a glutamate blocker is likely to prevent the excitotoxic process. Unfortunately, the glutamate blockers that are currently available have little use in a chronic treatment regimen since they are exceedingly toxic in their own right. Moreover, glutamate is ubiquitous throughout the nervous system as an excitatory transmitter. Thus, glutamate is not only involved in the communication among nerve cells associated with TD, but it is also involved with nerve cells that are not associated with any pathological process. The use of a glutamate blocker would indiscriminately interfere with all cellular communication involving glutamate, and could potentially disrupt normal functioning in non-pathological circuits.

Reports of attempts to reduce the side effects of haloperidol have been made. For example, U.S. Pat. No. 3,978,216 describes the use of a gabergic compound administered prior to or with a neuroleptic agent to reduce tardive dyskinesia; U.S. Pat. No. 4,316,897 reports that benzodiazepines can reduce serum prolactin when used with haloperidol; U.S. Pat. No. 3,505,451 relates that desipramine and imipramine reduce Parkinson-like symptoms in treating schizophrenia with haloperidol; and U.S. Pat. No. 4,582,823 discloses that adenosine derivatives used with haloperidol reduce the neurological side effects of schizophrenia treatment. Still, the problem of severe EPS and tardive dyskinesia continue to plague those individuals requiring chronic or life-long treatment for mental illness such as schizophrenia.

It is clear from the foregoing that another strategy is needed to circumvent the existing toxic effects stemming from the use of a variety of neuroleptics, as well as the eventual development of crippling side effects such as TD. A treatment for schizophrenia and other mental illnesses is needed to alleviate both the toxic effects of antipsychotic drugs and the onset of TD. The ideal agent to render neuroleptics benign, effective, and safe is a suitable drug, compound, or molecule, such as an amino acid or analogue thereof, for example, or a mixture of the abovementioned agents, that selectively blocks excitotoxicity without interfering with normal cellular communication mediated by glutamate. Because the toxic mechanism involved in cell death caused by overexcitation at glutamate synapses is a massive influx of calcium, the agent used for treatment should be an effective intracellular calcium buffer and should also block excitotoxicity. Until the present invention having a solid physicochemical foundation to support its efficacy, a safe and useful therapy for simultaneously treating schizophrenia and avoiding TD, with no other accompanying adverse effects, has not been available.

SUMMARY OF THE INVENTION

The present invention provides alternative and safe therapies for treating some CNS disorders and mental illnesses, particularly schizophrenia. The therapeutic method involves the use of therapeutic agents such as neuroleptics and antipsychotic drugs which are administered in combination with taurine, with precursors of taurine such as hypotaurine, with analogues of taurine, or with taurine derivatives or compounds having action similar to that of taurine. The invention is directed to co-administration of antipyschotic agents and taurine, and the like, resulting in an improvement over existing treatments so that severe side effects (in the form of severe EPS) are not experienced by patients undergoing chronic antipyschotic drug therapies.

Tardive dyskinesia is one important side effect which is alleviated by the present invention. Neuroleptics are administered concomitantly with the administration of taurine in unit dosage form to alleviate the physicochemical and biochemical events that are believed to be associated with the development of TD.

Administration of the neuroleptics and taurine can be carried out in any order, provided that one is supplied in effective amounts in conjunction with effective mounts of the other over the same relative period of time. Co-administration of a neuroleptic drug and taurine, or derivative thereof, means administration to a patient during a course of treatment. Frequently, co-administration occurs on a daily basis over an extended or long-term time period. As an example, a given neuroleptic drug and taurine, or derivative thereof, are administered on the same day, but each is administered at different times during the course of the day. Alternatively, the neuroleptic and taurine, and the like, are co-administered at one time of the day or they are co-administered at different times during the day. It is also envisioned that one neuroleptic drug, or suitable combinations of neuroleptics, may be administered with taurine, and the like, when feasible or warranted.

The invention further relates to a method of treating schizophrenia in a mammalian subject in the absence of neurological side effects, comprising administering to the subject effective amounts of a neuroleptic drug and taurine. The neuroleptic and taurine are in a pharmaceutically acceptable medium containing appropriate carriers and buffering components, if needed or desired, to achieve the desired effect. The present invention involves the use of other antipsychotic agents to be used in combination with taurine to treat schizophrenia without a concern for the late-occurring syndrome of TD and without the associated problem of agranulocytosis. The presence of taurine, or derivatives thereof, in combination with a particular neuroleptic drug, or suitable combinations of neuroleptic drugs, not only reduces or prevents the chance of developing TD, but also increases the efficacy of the neuroleptic drug used to treat schizophrenia or other CNS disorder which may be linked to the development of TD.

It an object of the present invention to use taurine, its precursor hypotaurine, or taurine derivatives, or compounds analogous to taurine, in combination with a neuroleptic or antipsychotic drug to treat schizophrenia, in particular, and to alleviate the side effect of TD.

It is another object of the invention to provide a means for alleviating the induction of TD caused by conventional neuroleptics, for example, haloperidol, which evoke a glutamate afflux whose excitotoxic action is unopposed by the other properties of these drugs, by co-administering a conventional neuroleptic drug with taurine to treat a mental illness such as schizophrenia. Conventional neuroleptics given in combination with taurine allay the development of TD. In addition, there is no evidence to suggest that this particular combination therapy regimen causes blood dyscrasias. Thus, combined administration of any one of the conventional neuroleptics with taurine in clinically effective doses and treatment regimens would have the benefits of therapy for schizophrenia with neither the well-documented associated risks nor the high costs of treatment with a drug such as clozapine, for example.

It is a further object of the invention to provide a new pharmaceutical composition comprising an antipsychotic drug and taurine, its precursor hypotaurine, taurine analogues, derivatives, or a similarly acting compound in a pharmaceutically-acceptable carrier for administration to schizophrenic patients to reduce, and preferably to alleviate, both the causes and the risk of developing the eventual side effect of TD.

The combination of antipsychotic drug and taurine in the present invention would have a profound impact on pyschiatric medicine and patients. For patients, the relief from the severely debilitating adverse neurological effect of TD promises to provide a more meaningful and less traumatic life. The combined anti-psychotic drug and taurine treatment has opened up a new biological perspective on the treatment of psychoses such as schizophrenia as a mental illness. Many schizophrenic patients who currently suffer from adverse behavioral, neurologic, metabolic, and endocrine effects as well as other toxic or allergic medical complications and reactions will benefit to a greater degree from the use of the present invention and its related innovations.

BRIEF DESCRIPTION OF THE DRAWINGS

FIG. 1A. Basal release (arrow indicates the dopamine peak; amplitude reflects magnitude of release). FIG. 1B. Cocaine (1 mg/kg), which potentiates dopamine by blocking uptake, increases dopamine. FIG. 1C. Haldol (i.e. haloperidol) caused increase similar to that of cocaine. FIG. 1D. Lack of postsynaptic effect of haldol on somatosensory striatal field potential. Upper trace: baseline response (pre-drug). Second trace: suppression of response caused by potentiation of dopamine's postsynaptic inhibitory effect via cocaine. Third trace: Haldol falls to attenuate the effects of dopamine. Arrow indicates time of somatosensory stimulus. Each trace represents an average of 16 trials. Time calibration is 5 milliseconds (ms).

FIGS. 4A and 4B. Schematic depiction of FIG. 4A) normal synaptic transmission mediated by glutamate; and FIG. 4B) depolarization of the neural membrane (i.e. excitation).

DETAILED DESCRIPTION OF THE INVENTION

Taurine

According to the present invention, the sulfonic amino acid taurine (2-aminoethanesulfonic acid) has been found to precisely perform several of the above described and desired functions of a therapeutic compound which serves to circumvent the toxicity of neuroleptics and to alleviate the development of TD associated with the administration of neuroleptics. In the present invention, taurine has been demonstrated to selectively block excitotoxicity without interfering with normal cellular interactions mediated by glutamate. Also, in accordance with the invention, taurine has been shown to be a very effective intracellular calcium buffer, and as such, prevented the massive calcium influx which is associated with overexcitation at glutamate synapses. Importantly, in the present invention, taurine has been shown to block excitotoxicity.

Taurine is widely distributed in living organisms and can arise via the decarboxylation of cysteic acid and/or via the oxidation of hypotaurine. Both intermediates can be formed from the amino acid cysteine (*Taurine*. Eds. R. Huxtable and A. Barbeau, Raven Press, New York, 1976) as shown by the following scheme:

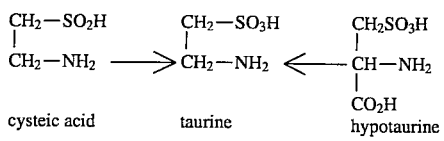

Many roles have been proposed for taurine and speculation abounds as to why taurine is present in very high levels in almost all mammalian tissues. However, the exact function(s) and modes of action of taurine remain elusive. Because taurine was found to be concentrated in selected areas of the brain, it has been theorized that taurine may be a neurotransmitter or that it may be a neuromodulator at some brain synapses. Diverse roles have been proposed for taurine, ranging from antiepileptic activity to stabilization of muscle intracellular membranes. However, the present invention is directed to a novel function and application for taurine. Until the present invention, taurine had not been implicated as an inhibitor of excitotoxicity which has been shown by the subject invention to be associated with the development of TD in schizophrenics treated with neuroleptics. Moreover, the use of taurine in conjunction with neuroantipsychotic drugs as a treatment and composition for preventing TD is singular to the present invention.

Figure 5A:
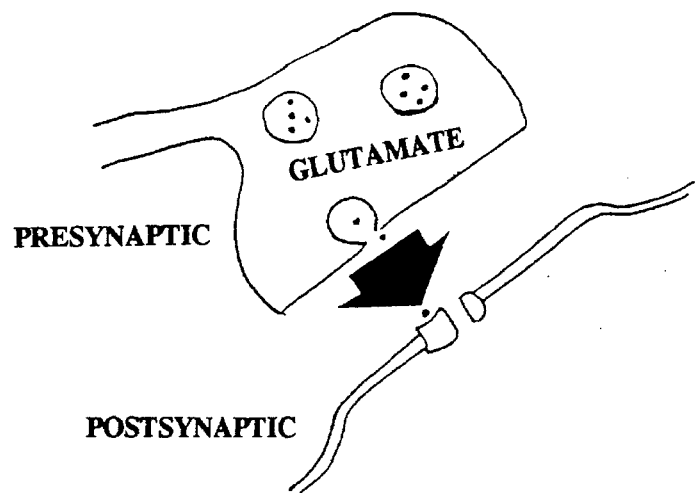
FIGS. 5A–5C. Schematic depiction of the excitotoxic effect of glutamate and the protective influences of taurine, or taurine-related compounds.
Figure 5B:
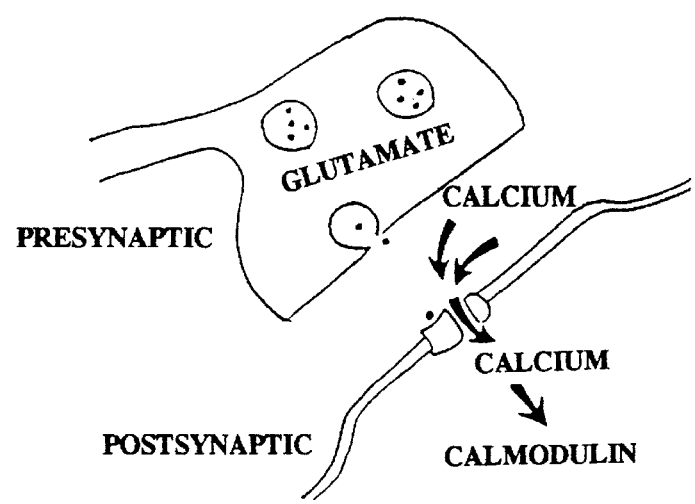
Figure 5C:
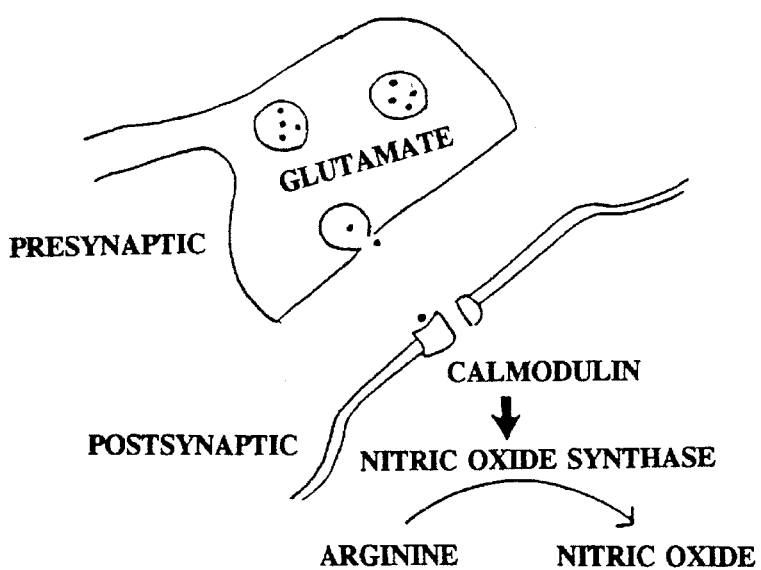

Normal synaptic transmission is mediated by glutamate which is released from axon terminals and binds to postsynaptic receptors (FIG. 4A). The opening of a calcium ion channel leads to an influx of calcium ions and depolarization of the neural membrane (i.e. excitation) (FIG. 4B). The enhanced effects of glutamate lead to an augmented calcium influx (FIG. 5A), which contribute to the excitotoxic effect of glutamate. In the case of neuroleptics, the enhancement of glutamate's effects is due to both presynaptic and to postsynaptic influences. The augmented calcium influx produces the following sequence of events: calcium ions bind to calmodulin (FIG. 5B); calmodulin activates nitric oxide synthase which catalyzes the conversion of arginine to the extremely toxic nitric oxide (FIG. 5C).

The protective influences of taurine in the above-described sequence of events are such that taurine acts as a calcium buffer during calcium flux (FIG. 5B) to prevent the binding of calcium ions to calmodulin, thus stopping the cascade of events leading to the production of nitric oxide, and ultimately preventing, inhibiting, or interfering with the excitotoxic process. It will be apparent to those skilled in the art that other protective agents, compounds, or molecules may also exert their effects at various downstream points in the series of steps leading to excitotoxicity, thereby resulting in action(s) similar to that of taurine. For example, prevention of the conversion of arginine to nitric oxide will also be protective and will preclude excitotoxicity. This latter prevention can be achieved by the use of nitric oxide synthase inhibitors such as methyl arginine and nitroarginine, for example.

Involvement of Neuroleptics with Dopamine Receptors and the Excitatory Amino Acid Glutamate The subject invention is intimately linked to the actions of neuroleptic drugs experimentally tested in an effort to understand the underlying causes of TD, a syndrome which accompanies the administration of known neuroleptic drugs. The invention provides and is based on a pharmacochemical explanation of the causes of TD associated with neuroleptic medications for schizophrenia. The invention is concerned with a valid, neurophysiological explanation for the underlying causes of TD stemming from the blocking action of dopamine receptors and linked to the administration of neuroleptic drugs.

Recent evidence has shown that anti-psychotic drugs may cause brain damage by an indirect but potentially lethal route. For example, damage to nigrostriatal terminals is believed to be a consequence of the neuroleptic agents haloperidol, a dopamine antagonist, as well as methamphetamine, which is a stimulant of the central nervous system. However, specific diagnostic signs of both neuroleptic- and methamphetamine induced damage, as evidenced in electronmicrographs, are absent when the N-methyl-D-aspartate (NMDA) ionophore blocking agent MK-801 is co-administered with haloperidol. NMDA is a subclass of glutamate receptors which is blocked by MK-801.

Although methamphetamine and haloperidol have quite different pharmacological actions, they are similar in terms of their end results with respect to dopamine. Both methamphetamine and haloperidol (as well as other neuroleptic drugs) cause the release of dopamine. The present inventor has concluded, based on experimentation and the evaluation of existing evidence, that neurotoxicity induced by neuroleptics involves dopaminergic interactions with the excitatory amino acid glutamate. Such a causative link between dopamine and glutamate has heretofore not been suggested.

The substrate of the interaction between dopamine and glutamate has been identified by anatomical and pharmacological data. Nigrostriatal axons synapse on the terminals of corticostriatal fibers which release glutamate. The postsynaptic dopamine receptor is likely to be of the $D_2$ type, since cortical lesions result in a marked reduction of these receptors within the striatum after terminal degeneration has occurred (De Keyser, J. and Ebinger, G. Neostriatal dopamine receptors. *Trends in Neurosci.*, 13: 324–325 (1990)).

The nature of the influence of haloperidol on glutamatergic terminals is discussed hereinbelow. It has been firmly established that glutamate has strong cytotoxic effects in a variety of pathological states (e.g. anoxia). Supranormal postsynaptic responses to glutamate trigger an influx of calcium ions that can cause cell death by activation of proteases and lipases, by damage to mitochondria, and by the formation of nitric oxide.

The present invention is related to the finding that in order for a neuroleptic such as haloperidol to have toxic effects via glutamate, the release or postsynaptic effects of glutamate must be enhanced. In accordance with the evidence imparted herein, haloperidol may increase glutamate release by one of several mechanisms. One mechanism is operative if dopamine has an inhibitory effect on glutamate afflux. If this is the case, then haloperidol's blockade of $D_2$ receptors on corticostriatal terminals is likely to result in disinhibition. A second type of mechanism is operative if dopamine has effects on corticostriatal glutamate release which relates to the duration of the action rather than to the amount of neurotransmitter released. Notwithstanding, glutamate is removed from the synaptic cleft by a sodium-dependent, high-affinity uptake system, thereby terminating its postsynaptic actions. It has been shown that dopamine and dopamine agonists inhibit this uptake system and thereby prolong the post-synaptic actions of glutamate (Kerkerian, L., Dusticier, N. and Nieoullon, A. Modulatory effect of dopamine on high-affinity glutamate uptake in the rat striatum. *J. Neurochem.*, 48: 1301–1306 (1987)). Still another mechanism for dopamine effecting toxicity via glutamate has recently been identified. Dopamine augments the effect of glutamate at the NMDA receptor. The increased excitatory action of glutamate mediated by dopamine would therefore increase its excitotoxic potential (Knapp, A. G., Schmidt, K. F. and Dowling, J. E. Dopamine modulates the kinetics of ion channels gated by excitatory amino acids in retinal ganglion cells. *Proc. Natl. Acad. Sci., USA*, 87: 767–771 (1990); Knapp, A. G. and Dowling, J. E. Dopamine enhances excitatory amino acid-gated conductances in cultured retinal horizontal cells. *Nature*, 325: 437–439 (1987)).

The present invention is directed to the following sequence of events which underlies the development of TD: Neuroleptic drugs block presynaptic dopamine receptors and result in increased release of dopamine. In turn, dopaminergic stimulation of corticostriatal terminals blocks glutamate re-uptake and, in conjunction with the interactions of dopamine with NMDA receptors, potentiates glutamate's postsynaptic actions. Finally, glutamatergic transmission results in an excitotoxic action in the striatum. Excitotoxicity leads to damage to nigrostriatal terminals and to a loss of striatal output neurons displaying receptors for the synaptic transmitter gamma-aminobutyric acid (GABA). Evidence to support the latter type of damage is found in electronmicrographic signs of striatal cell loss and in the detection of GABA receptor supersensitivity in the targets of striatal output, following chronic use of haloperidol as an exemplary neuroleptic agent (Jeste, D. V., Lohr, J. B. and Manley, M. Study of the neuropathologic changes in the striatum following 4, 8 and 12 months of treatment with fluphenazine in rats. *Psychopharmacol.*, 106: 154–160 (1992); Frey, J. M., Ticku, M. K. and Huffman, R. D. GABAergic supersensitivity within the pars reticulata of the rat substantia nigra following chronic haloperidol administration. *Brain Res.*, 425: 73–84 (1987)). Loss of striatal neurons, damage of nigrostriatal terminals, or some combination of the two, would produce sufficient disruption of striatal motor functioning to produce the symptoms of TD.

Figure 6:
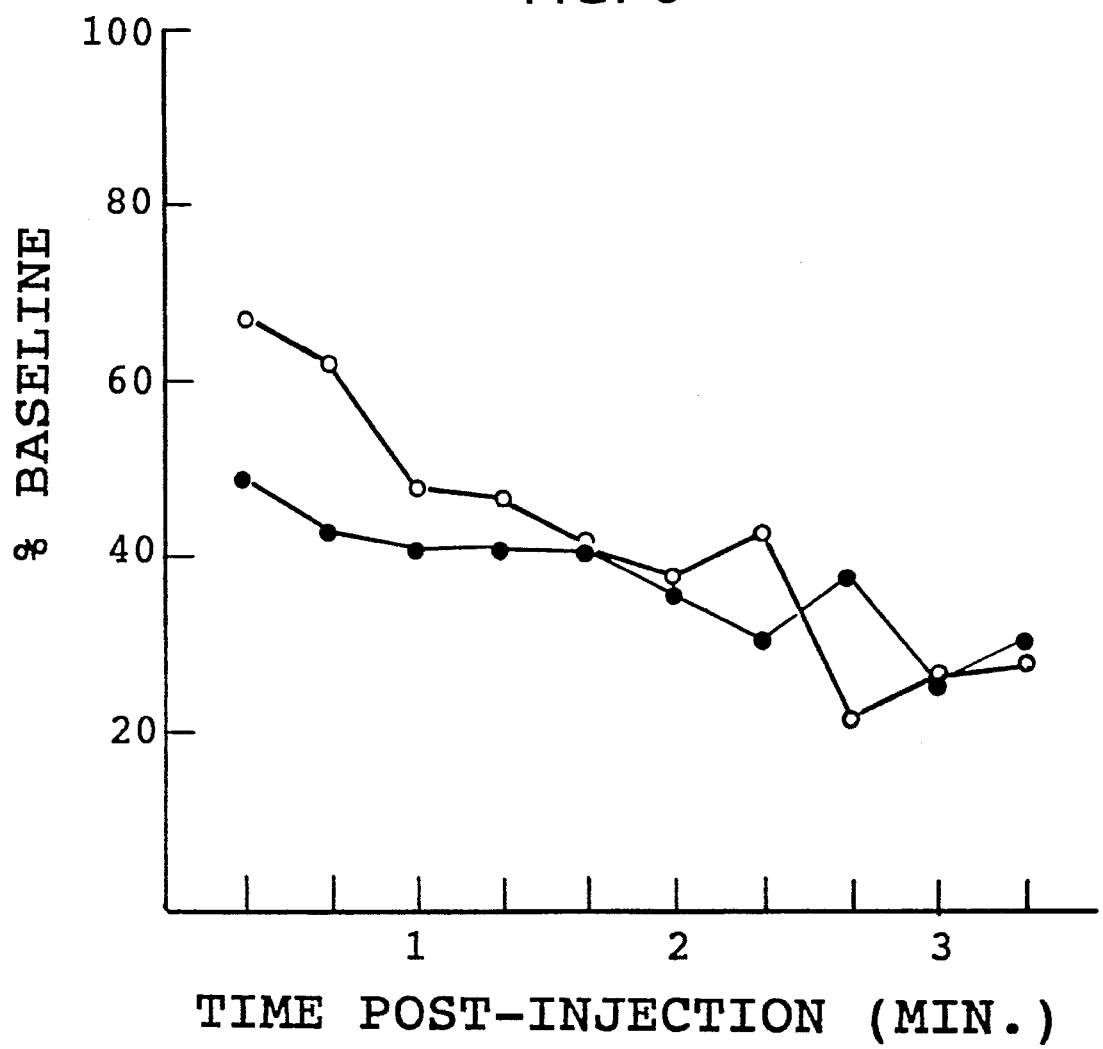
FIG. 6. The effects of haloperidol or haloperidol co-admininstered with taurine on striatal field potentials. Field potentials were evoked in the striatum by somatosensory stimulation. Intravenous administration of haloperidol (0.2 mg/kg), (filled circles), suppressed these responses compared with the magnitude of the responses prior to drug administration ("BASELINE"). Co-administration of taurine (10 mg/kg; intravenous), (open circles), with haloperidol also resulted in suppression. No significant differences were observed between the effects of haloperidol compared with haloperidol plus taurine.

Co-administration of taurine with a neuroleptic such as haloperidol did not interfere with those electrophysiological effects of the neuroleptic that are mediated by dopamine (see FIG. 6). Such a finding is important since it means that taurine, or derivatives thereof, are not expected to interfere with the antipsychotic potency of the neuroleptic drug. Indeed, the suppression caused by haloperidol as shown in FIG. 6 is mediated by the dopaminergic effect of this drug (Lidsky, T. I. and Banerjee, S. P. Clozapine's mechanisms of action: non-dopaminergic activity rather than anatomical selectivity. *Neurosci. Letters*, 136: 100–103 (1992)). Since the dopaminergic effect of a neuroleptic drug such as haloperidol underlies its antipsychotic potency, the results shown in FIG. 6 indicate that it is unlikely that taurine, and derivatives thereof, will diminish the clinical usefulness of the neuroleptic drug.

One embodiment of the present invention provides modified, safe anti-psychotic drug regimens for the treatment of schizophrenia by employing conventional neuroleptics, for example, haloperidol, in combination with taurine, and the like, to minimize the dangers of TD. In view of the seminal role of calcium in the excitotoxic process, attenuation of the actions of calcium by taurine specifically in excitotoxicity offers a plausible and sound explanation for the prevention of TD during treatments employing effective amounts of a variety of anti-psychotic drugs in conjunction with the administration of taurine. Hypotaurine, a precursor of taurine, a number of natural and synthetic derivatives of taurine, and similarly-acting compounds or suitable analogues of taurine can also be used in the present invention. Other compounds and taurine derivatives, which act in a manner similar to that of taurine and which may be used in the present invention, are exemplified by, but not limited to, the following: 5 β-taurocholenic acids and 5 β-taurocholadienic acids (described in U.S. Pat. No. 3,580,936, issued May 25, 1971 to A. A. Patchett and J. Hannah), L-gamma-glutamyl taurine (described in U.S. Pat. No. 4,226,884, issued Oct. 7, 1980 to L. Feuer), taurine-containing peptides of the formula:

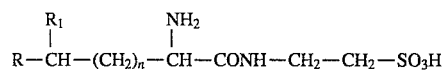

described in U.S. Pat. No. 4,795,595, issued Jan. 3, 1989), taurinamide (described in U.S. Pat. No. 4,840,964, issued Jun. 20, 1989 to M. G. Di Schiena), phthalyltaurine (described in U.S. Pat. No. 4,556,673, issued Dec. 3, 1985 to L. H. Andersen), sulfonamide derivatives of taurine, taurine derivatives represented by the general formula:$(CH_3-CO-NH-CH_2-CH_2-SO_3)_n-M^+$, where M is an alkali metal such as $K^+$, $Li^+$, or an alkaline earth metal of valence n, with n=1 or 2, such as $Ca^{++}$, $Mg^{++}$, or $Mn^{++}$ (described in U.S. Pat. No. 4,199,601, issued Apr. 22, 1980 to J. P. Durlach; in U.S. Pat. No. 4,267,194, issued May 12, 1981 to J. P. Durlach; and in U.S. Pat. No. 4,271,189, issued Jun. 2, 1981 to J. P. Durlach), or N-acetyl-L-aspartyltaurine (described in U.S. Pat. No. 4,593,045, issued Jun. 3, 1986 to M. Flork and A. Bigou).

It should be noted that although taurine is a sulfonate analogue of β-alanine, the sulfonic acid function of taurine provides taurine with different physicochemical properties from those of β-alanine, which is a putative inhibitory neurotransmitter (R. Huxtable. Metabolism and Function of Taurine in the Heart. In: *Taurine*. Eds. R. Huxtable and A. Barbeau, Raven Press, New York, 1976). Indeed, when β-alanine was administered to rats on a daily basis for 21 days, either in conjunction with haloperidol or by itself, β-alanine failed to protect against the effects of chronic haloperidol treatment. In addition, when administered alone, β-alanine appeared to have deleterious effects in the striatum of experimental animals.

Another embodiment provides taurine co-administered in a pharmaceutical composition with any conventional neuroleptic drug in a pharmaceutically-acceptable carrier and in an amount sufficient to provide both effectual anti-psychotic potency and reduced liability to TD.

Doses

The range of effective doses among various neuroleptics administered to adult patients is quite broad. Even with individual drugs in each class of drugs (e.g. phenothiazines, piperazine, thioxanthene, butyrophenone, dibenzoxazepine, dihydroindolone, and dibenzodiazepine), a wide range of doses may be used, since therapeutic margins are substantial. Assuming that doses are equivalent, there is no evidence that any anti-psychotic drug is superior in overall efficacy to any other. However, some patients who fail to respond to one drug may respond to another, and for this reason, several drugs may have to be tried to find the one most effective for an individual patient. Some seemingly refractory patients have responded to larger-than-usual doses of the more potent anti-psychotics, such as 100 mg/d of haloperidol or 200 to 300 mg/d of thiothixene. In many cases, drug doses should be tried on an experimental basis before it is concluded that a patient will not respond to drug therapy. For mammaliam subjects, the dosage ranges can vary greatly. Dosages may range from about 0.1 to about 2000 mg per kilogram of body weight per day, or preferably between about 1 mg/kg to about 500 mg/kg of body weight per day, more preferably between about 10 mg/kg to about 250 mg/kg, depending on the particular neuroleptic administered, route of administration, dosage schedule and form, and general and specific responses to the drug. For convenience, the total daily dosage may be divided and administered in portions throughout the day, if desired.

Some dose relationships between various neuroleptic drugs, as well as possible ranges, are shown below in TABLE 1:

TABLE 1

| Dose Relationships of Neuroleptics | | |
|---|---|---|
| | MINIMUM EFFECTIVE THERAPEUTIC DOSE (mg) | USUAL RANGE OF DAILY DOSES (mg) |
| Chlorpromazine (Thorazine) | 100 | 100–1000 |
| Thioridazine (Mellaril) | 100 | 100–800 |
| Mesoridazine (Lidanar, Serentil) | 50 | 50–400 |
| Piperacetazine (Quide) | 10 | 20–160 |
| Trifluoperazine (Stelazine) | 5 | 5–60 |
| Perphenazine (Trilafon) | 10 | 8–64 |
| Fluphenazine (Permitil, Prolixin) | 2 | 2–20 |
| Thiothixene (Navane) | 2 | 2–120 |

TABLE 1-continued

| Dose Relationships of Neuroleptics | | |
|---|---|---|
| | MINIMUM EFFECTIVE THERAPEUTIC DOSE (mg) | USUAL RANGE OF DAILY DOSES (mg) |
| Haloperidol (Haldol) | 2 | 2–20 |
| Loxapine (Loxitane) | 10 | 20–160 |
| Molindone (Lidone, Moban) | 10 | 20–200 |
| Clozapine (Clozanil) | 50 | 25–400 |

Taurine may be administered in a range of from about 0.1 mg/kg of body weight to about 2500 mg/kg of body weight, preferably from about 0.5 mg/kg to about 250 mg/kg, more preferably from about 5 mg/kg to about 150 mg/kg. For example, in humans, taurine may be provided in capsular form containing 250 mg of taurine. Treatment with neuroleptics may be started using one dose of taurine (e.g. 250 mg/day) and taurine doses may increase at periodic intervals (e.g. once a week in increments of 250 mg) in divided doses up to a daily maximum dose (e.g. about 2 g/day). Mean daily doses are close to about 1,500 mg of taurine. Oral doses of taurine may be administered in an mount of about 0.5 g to about 1.5 g per day. It will be evident to one skilled in the art that although taurine analogues and derivatives may be used at the same doses as taurine in its naturally-occurring form, other doses may be appropriate for such analogues, derivatives, and similar compounds, and may be experimentally or clinically determined. When taurine has been used at high levels in an effort to treat epileptic seizures, no side effects attributable to taurine could be demonstrated, apart from a few cases of somnolence (A. Barbeau, Tsukada, Y., and Inoue, N. Neuropharmacologic and behavioral effects of taurine. In: *Taurine*, Eds. R. Huxtable and A. Barbeau, Raven Press, New York, (1976), pp. 253–266). Thus, toxicity due to taurine is not a problem. Although the dose ranges provided are meant as a guide for one skilled in the art, optimum dosages can be determined clinically, and other doses may be equally suitable or permitted, if effective.

Plasma Concentrations and Clinical Effects

Attempts to define a therapeutic range of plasma concentrations of neuroleptic agents are beset by many difficulties. Although a range of about 150 ng/mL to about 300 ng/mL has been suggested for chlorpromazine, this range is tenuous. Ranges of 4 to 20 ng/mL have been suggested for haloperidol; however, some very refractory patients may benefit from levels up to 50 ng/mL. If necessary or desired, clinical monitoring of plasma concentrations of these drugs may be undertaken.

Pharmaceutical Preparations

The combination of the neuroleptic agent and taurine is administered in effective mounts either parenterally or orally either alone in succession, together, or in the form of pharmaceutically-acceptable preparations containing the neuroleptic and taurine as the active agents of the invention to achieve the desired effect. Well-tolerated parenteral forms of the high-potency drugs are available for rapid initiation of treatment as well as for maintenance treatment in noncompliant patients. Since the parenterally-administered drugs may have much greater bioavailability than the oral forms, doses may be only a fraction of what would be given orally.

Pharmaceutical preparations containing neuroleptics and taurine and conventional pharmaceutical carriers may be employed in unit dosage forms such as solids or liquids. Solid form preparations include, for example, tablets, pills, capsules, powders, dispersible granules, cachets, and suppositories. Liquid form preparations include isotonic solutions, suspensions, or elixirs for oral administration or liquid solutions, suspensions, and emulsions for parenteral use. The unit dosage form can be a packaged preparation, the package containing discrete quantifies of preparation, for example, packeted tablets, capsules, and powders in vials or ampules. The unit dosage form can also be a capsule, cachet, or tablet itself, or it can be the appropriate number of any of these in packaged form. As an exemplary guide, for oral administration, taurine as an active ingredient in a composition with a neuroleptic drug(s) for humans, is provided at the unitary dose of about 0.30 g to about 1.0 g for capsules, sugar-coated pills, tablets, gelatin-coated capsules, and from 3 to 5 g/10 mL for solutions. Tablets contain the active ingredient in admixture with non-toxic, pharmaceutically-acceptable excipients which are suitable for the manufacture of tablets. These excipients may be, for example, inert diluents, for example, calcium carbonate, sodium carbonate, lactose, calcium phosphate or sodium phosphate; granulating or disintegrating agents, for example, maize starch or alginic acid; binding agents, for example, starch, gelatin, or acacia; and lubricating agents, for example, magnesium stearate or stearic acid. The tablets may be uncoated or they may be coated by known techniques to delay disintegration and absorption in the gastrointestinal tract, and thereby provide a sustained action for a longer period of time.

The composition may be formed by dispersing the components in a suitable pharmaceutically-acceptable liquid or solution such as sterile physiological saline or other injectable aqueous liquids. The composition may be administered parenterally, including subcutaneous, intravenous, intramuscular, or intrasternal routes of injection or infusion techniques, although conventionally via subcutaneous or intramuscular routes of injection. For parenteral administration, the composition is in sterile solution or suspension or may be emulsified in pharmaceutically- and physiologically-acceptable aqueous or oleaginous vehicles, which may contain preservatives and material for rendering the solution or suspension isotonic with body fluids (i.e. blood) of the recipient. Such formulations may be used in unit-dose or in multi-dose containers for convenience. Excipients suitable for use are water, phosphate buffered saline, pH 7.4, 0.15M aqueous sodium chloride solution, dextrose, glycerol, dilute ethanol, and the like, and mixtures thereof.

If oral administration is desirable or required, the composition may be presented as a draught in water or in a syrup, in capsules, cachets, boluses, or tablets, as an aqueous or oleaginous solution or suspension, or a suspension in a syrup. Such suspensions optionally may include suspending agents, or may be presented as an oil-in-water or water-in-oil emulsion. Where desirable or necessary, flavoring, sweetening, preserving, emulsifying, or thickening agents may be included in the formulation. Examples of sweetening agents are glycerol, sorbitol, or sucrose. Such formulations may also contain a demulcent and coloring agents. Formulations for oral use may also be presented as hard gelatin capsules wherein the active ingredient is mixed with an inert solid diluent, for example, calcium carbonate, calcium phosphate, or kaolin, or as soft gelatin capsules, wherein the active ingredient is mixed with an oil medium, for example, arachis oil, liquid paraffin, or olive oil. Additional formulations suitable for other modes of administration such as suppositories may include binders and carriers, for example, polyalkalene glycols or triglycerides.

Tablets may contain the preparation as a powder or granules, for example, a lyophilized powder or granules optionally mixed with binders, lubricants, inert diluents, or surface-active or dispersing agents, and may be formed by compression or by mouling in inert liquid diluent. Such tablets may be optionally scored and/or coated. Capsules and cachets may contain the active compound(s) alone or in admixture with one or more accessory ingredients. Capsules may also contain the active ingredients in aqueous or oleaginous solution, suspension, or emulsion, optionally in association with accessory ingredients. Presented in unit dosage form, each dose may be conveniently contained in, but is not limited to being contained in, volumes of from about 0.1 mL to about 1.0 mL, preferably about 0.5 mL.

Aqueous suspensions contain the active ingredients in admixture with excipients suitable for the manufacture of aqueous suspensions. Such excipients are suspending agents, for example, sodium carboxymethyl cellulose, methylcellulose, hydroxypropylmethylcellulose, sodium alginate, polyvinylpyrrolidone, gum tragacanth, and gum acacia; dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol, for example, polyoxyethylene sorbitol monooleate, or condensation products of ethylene oxide with partial esters derived from fatty acids and hexitol anhydrides, for example, polyoxyethylene sorbitan monooleate. The aqueous suspensions may also contain one or more preservatives, for example, ethyl or n-propyl p-hydroxy benzoate, one or more coloring agents, one or more flavoring agents, and one or more sweetening agents, such as sucrose, saccharin, or sodium or calcium cyclamate.

Dosage Schedules

Neuroleptics may be administered in divided daily doses initially while an effective dose level is being sought. The drugs need not be given in equally-divided doses, even when given orally. After an effective daily dose has been defined for an individual patient, the appropriate doses may be given less frequently. Once-daily doses, usually given at night, are feasible for many patients during chronic maintenance treatment. Simplification of dosage schedules leads to better compliance. Maximum dose units of many drugs are being increased by manufacturers to meet the needs of once-daily drug dosing.

The quantity of compounds administered can vary over a wide range to provide from about 0.1 mg/kg to about 300 mg/kg, for example, of body weight of the patient per day. Unit doses of the neuroleptic and taurine components of the invention can contain, for example, from about 50 mg to about 2000 mg of the components and may be administered from one to several times daily, as an example. The dosages may be varied depending on the requirements of the individual patient, the severity of the condition being treated, and the administration regimen being followed. Determination of the proper dosage for a particular situation is within the skill of the art.

Maintenance Treatment

A small minority of schizophrenic patients may remit from an acute episode and require no further drug therapy for prolonged periods. However, in most cases, schizophrenia is a chronic disorder that only partially remits so that drug therapy, included the combined drug therapy as disclosed herein, must be continued indefinitely.

EXAMPLES

The invention is further demonstrated by, but is not intended to be limited to, the following illustrative examples:

Example I

Effects of Taurine on Dysfunctions Caused by Chronic Haloperidol Administration

I. Decreases in Striatal Dopamine

There are several alterations in the normal functioning of the dopamine system that are caused by repeated treatments with antipsychotic drugs. The present invention presumes that these changes are the initial events in the cascade that finally culminates in the development of TD. Among all of the antipsychotics, only clozapine produces neither TD nor the above-mentioned alterations. Notwithstanding, one change that is very likely to lead to the onset of TD is a decrease in dopamine levels in nigrostriatal axon terminals in the striatum.

Figure 1A:
FIGS. 1A–1D. Dopamine release measured by microdialysis and analyzed by high pressure liquid chromatography (HPLC) with electrochemical detection.
Figure 1B:
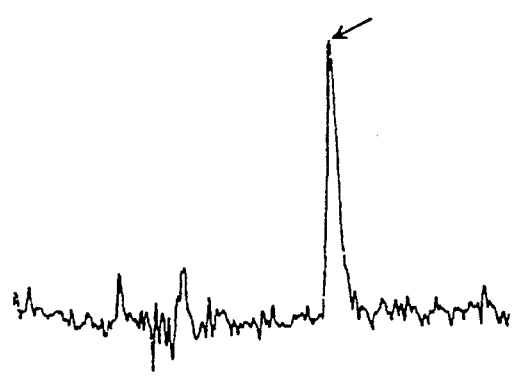
Figure 1C:
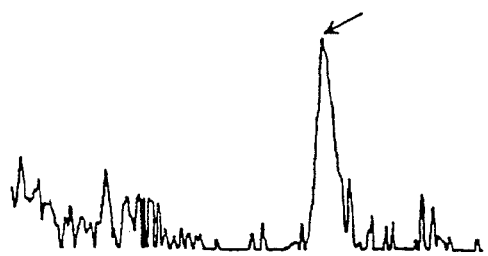
Figure 1D:
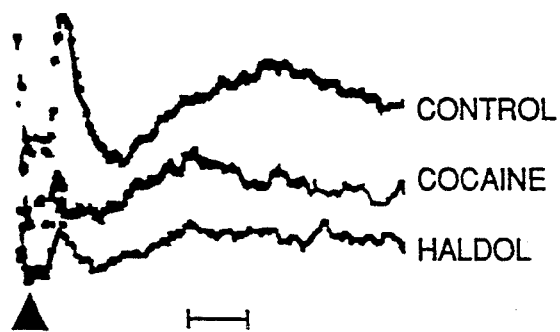
Figure 2:
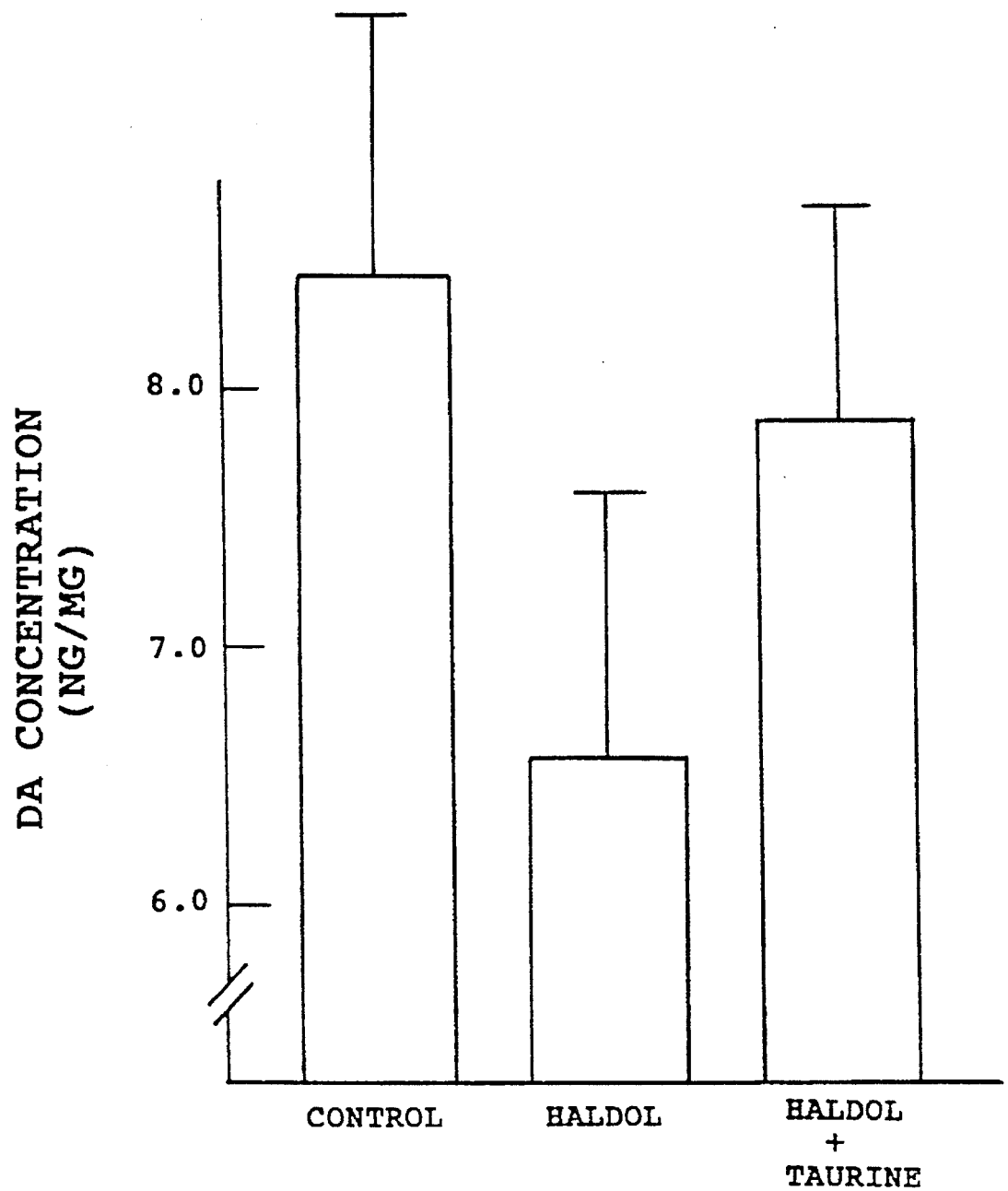
FIG. 2. Effects of chronic haldol (i.e. haloperidol) administration on striatal dopamine levels. Taurine co-administered with haldol ameliorated the dopamine depletion caused by haldol. Both control and the haldol+taurine groups differed from the haldol group (t test; $p<0.01$). Haldol+taurine and control groups did not significantly differ from each other ($p>0.05$). Y-axis: DA, dopamine concentration in nanograms/milligram (ng/mg).

To test the efficacy of co-administering taurine with antipsychotic drugs, in vivo experiments were performed in mammals. Accordingly, three groups of rats were tested. One group, which served as the Control, received no drugs. The second animal group received daily intraperitoneal injections of 0.5 mg/kg of haloperidol. The third group received both 0.5 mg/kg of haloperidol and 100 mg/kg of taurine. After 21 days of treatment, the dopamine levels in the striatum of the three groups of animals were analyzed by high performance liquid chromatography (HPLC) with electrochemical detection. Haloperidol treatment caused a statistically significant decrease in striatal dopamine. In contrast, animals receiving injections of both haloperidol and taurine had completely normal dopamine levels (see FIG. 2).

Example II

Effects of Taurine on Dysfunctions Caused by Chronic Haloperidol Administration

I. Increases in $D_2$ Receptors

Figure 3:
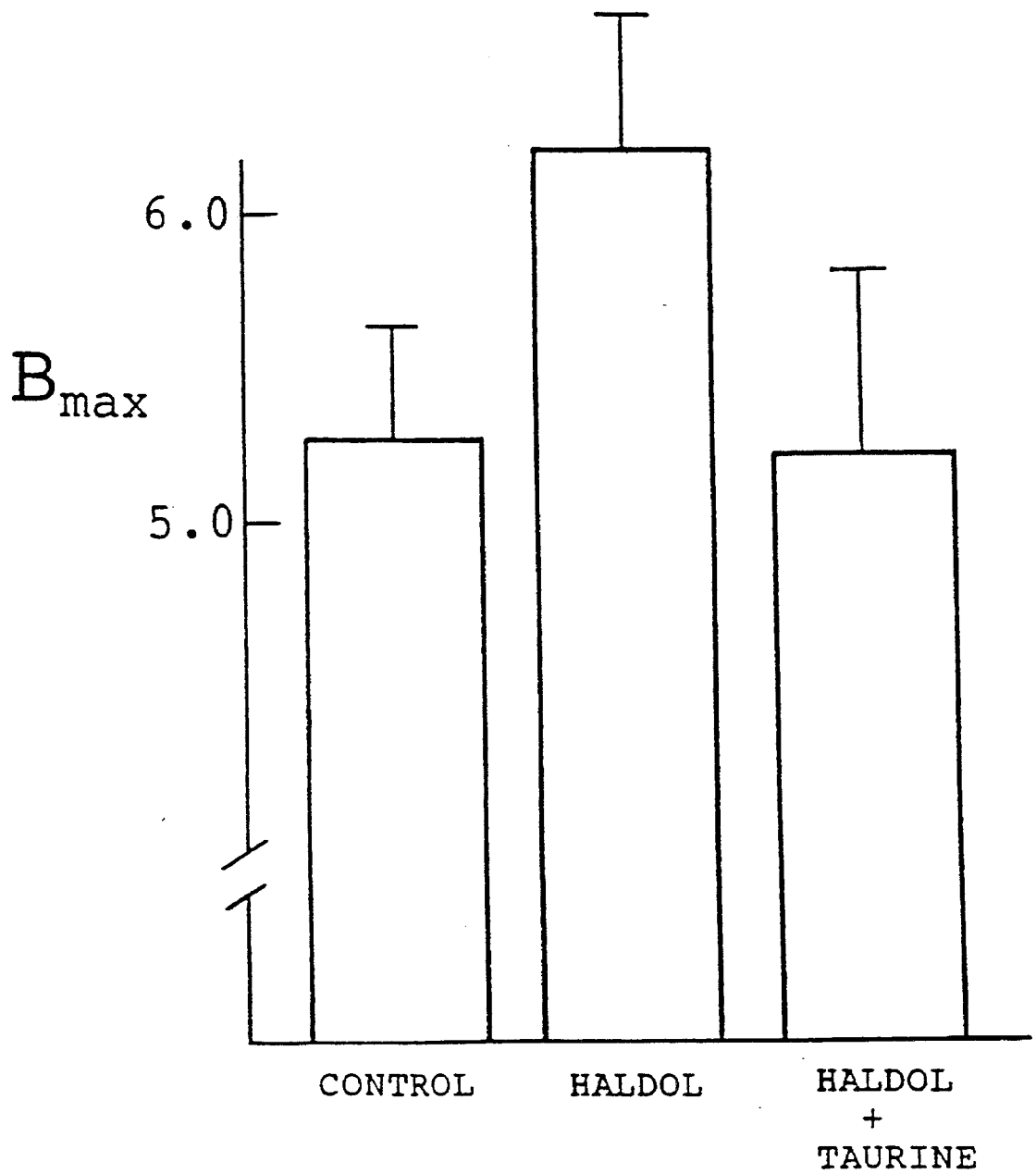
FIG. 3. Effects of chronic haldol (i.e. haloperidol) administration on the number of striatal $D_2$ receptors ($\times 10^{-14}$/mg; wet weight). Co-administration of taurine with haldol completely prevented the increase in $D_2$ receptors seen with haldol alone.

Mother dysfunction caused by chronic medication with antipsychotic drugs is a proliferation in $D_2$ dopamine receptors in the striatum. One result of this increase is the development of behavioral supersensitivity wherein stimulation with exceedingly low levels of dopamine produces abnormal movements. To determine if taurine co-administration was effective in this context, in vive experiments were conducted in mammals. Three groups of rats were tested. One group which served as Controls received no drugs. A second group received daily intraperitoneal injections of haloperidol at 0.5 mg/kg. A third group received both 0.5 mg/kg of haloperidol and 100 mg/kg of taurine. After 21 days of treatment, in vitro receptor binding assays were performed in striatal homogenates to determine the numbers of $D_2$ receptors. In comparison to the controls, the animals receiving haloperidol had elevated numbers of $D_2$ receptors. In contrast, the number of $D_2$ receptors in animals receiving taurine co-administered with haloperidol was the same as that of the control animals (see FIG. 3).

Example III

The effectiveness of the co-administration of taurine and a given neuroleptic drug is demonstrated in an in vive animal model of tardive dyskinesia. Four groups of male Sprague-Dawley rats are tested. Since neuroleptic drug treatment must be maintained throughout the lifetime of the schizophrenic individual, animals are treated daily for an extended period of time. Accordingly, one group of from three to six animals is treated daily with haloperidol as the neuroleptic drug. Another group of animals is treated with a placebo, or physiological buffer or saline alone and serves as a control group (i.e. no drug control group). Alternatively, or in addition to the placebo-treated control animals, another group of control animals may remain untreated and monitored in parallel with the treated control and the experimental animals. A third group of animals is treated with daily doses of taurine, a taurine analogue or derivative, or a similarly-acting compound. A fourth group of animals receives both haloperidol in combination with taurine. Treatment preferably occurs for about twelve months or longer (e.g. eighteen or more months). Haloperidol in the lactate form is readily soluble in water, as is taurine and its equivalents, and is administered orally as pan of the diet. The concentrations of drug and taurine are adjusted so that the average daily water intake of the animals corresponds to 0.5 mg/kg of haloperidol and 100 mg/kg of taurine. Thus, the chronic treatment is safe, non-traumatic, and efficiently ongoing. Parenteral injections may be administered, if desired or necessary.

It has been shown that after chronic treatment with a neuroleptic drug such as haloperidol, animals which have been exposed to the neuroleptic drug exhibit loss of neurons in the striatum, and also exhibit "vacuous jaw movements", which are spontaneous jaw movements made without apparent reason and in the absence of any type of stimulation. The manifestations of nerve cell loss and vacuous jaw movements serve as indicators or phenotypic markers of tardive dyskinesia in these animals.

Striatal cell loss is measured as described in Jeste, D. V., Lohr, J. B. and Manley, M. Study of the neuropathologic changes in the striatum following 4, 8 and 12 months of treatment with fluphenazine in rats. *Psychopharmacol.*, 106: 154–160 (1992). Briefly, experimental animals are sacrificed at the termination of the experimental period, the brain is removed, and coronal sections through the striatum of the brain are examined by light microscopy. Computer controlled methodologies known to those in the art are used for scanning such sections and for counting individual cells. Jaw movements are measured in two ways. In the first method, electromyograph (EMG) electrodes are implanted in the jaw opening (digastric) and jaw closing (masseter) muscles. Electrical recordings of muscle contractions are stored on tape and are subjected to computer analysis for quantification in terms of frequency and magnitude of contractions. In the second method, the movements of the animals are recorded on videotape and the movements are counted by observers who are unaware of the experimental treatment received by the animals.

In the present experiment in mammals, the animals receiving long-term administration of haloperidol show oven signs of vacous jaw movements and striatal nerve cell loss at the end of approximately one year of treatment. The placebo-treated and control animals, and the taurine alone-treated animals show neither signs of EPS nor neuronal degeneration or death. Evidence of the effectiveness of the co-administration of haloperidol and taurine is a significant absence of striatal cell loss and an absence of the loss of motor functioning in the form of vacuous jaw movements, in contrast to the occurrence of these conditions in the animals receiving haloperidol alone.

Based on the findings as disclosed in the Examples above, taurine, and derivatives thereof, is completely effective in preventing the dysfunctions caused by chronic treatment with haloperidol. Therefore, conventional neuroleptics would be rendered benign with respect to TD if given in conjunction with taurine. Moreover, there have been no reports or evidence which suggest that taurine causes blood dyscrasias. Thus, the risk of developing agranulocytosis or other dyscrasia from the use of treatment involving the combination of a neuroleptic and taurine is virtually nil. The combined administration of any of the conventional neuroleptics with taurine appears to have the benefits of an effective therapy for the treatment of schizophrenia and TD without the profound risks which accompany the use of clozapine.

The contents of the references contained herein are hereby incorporated by reference.

Although the foregoing invention has been described in some detail by way of illustration and example for purposes of clarity of understanding, it will be obvious to those skilled in the art that certain changes and modifications may be practiced without departing from the spirit and scope thereof, as described in the specification and as defined in the appended claims.

What is claimed is:

1. A pharmaceutical composition for preventing the development of tardive dyskinesia in a patient, comprising a combination of a $D_2$ receptor-blocking neuroleptic drug and taurine, or derivatives thereof, in a pharmaceutically-acceptable carrier.

2. The composition according to claim 1, wherein said neuroleptic drug is haloperidol.

3. The composition according to claim 1, wherein said composition is in unit dosage form.

4. The composition according to claim 3, wherein said composition comprises from about 50 mg to about 2000 mg per unit dose of said drug and taurine.

5. The composition according to claim 3, wherein said composition is in oral unit dosage form.

6. The composition according to claim 3, wherein said composition is in injectable unit dosage form.

7. A method of treating a patient for schizophrenia, which comprises administering to said patient an effective amount of said pharmaceutical composition according to claim 1, said composition having the ability to prevent the development of the side effect of tardive dyskinesia in said patient.

8. A method for treating a patient for a central nervous system disorder associated with psychotic behaviour or dementia, which comprises administering to said patient a combination of a therapeutically effective amount of a $D_2$ receptor-blocking neuroleptic drug and a therapeutically effective amount of taurine, or analogues thereof, said combination having the ability to reduce the development of the neurological side effect of tardive dyskinesia in said patient.

9. The method according to claim 8, wherein said central nervous system disorder is schizophrenia.

10. The method according to claim 1, wherein said neuroleptic drug is selected from the group consisting of chlorpromazine, haloperidol, thioridazine, mesoridazine, piperacetazine, trifluoperazine, perphenazine, fluphenazine, thiothixene, loxapine, molindone, and any drug known as a major tranquilizer, neuroleptic, or antipsychotic, or mixtures thereof.

11. The method according to claim 10, wherein said neuroleptic drug is haloperidol.

12. A method of treating a patient for schizophrenia, which comprises administering to said patient a combination of a therapeutically effective amount of a $D_2$ receptor-blocking antipsychotic drug and a therapeutically effective amount of taurine, a taurine precursor, a taurine derivative, or a compound similar in action to taurine, said combination having the ability to reduce the development of the side effect of tardive dyskinesia in said schizophrenic patient.

13. The method according to claim 12, wherein said precursor of taurine is hypotaurine.

14. The method according to claim 12, wherein said taurine derivative is selected from the group consisting of 5 β-taurocholenic acids, 5 β-taurocholadienic acids, L-gamma-glutamyl taurine, taurine-containing peptides of the formula:

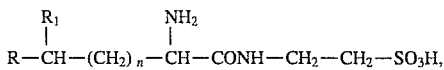

taurinamide, phthalyltaurine, sulfonamide derivatives of taurine, taurine derivatives represented by the general formula: $(CH_3-CO-NH-CH_2-CH_2SO_3)_n-M^+$, where M is an alkali metal or an alkaline earth metal of valence n, wherein n=1 or 2 and N-acetyl-L-aspartyltaurine.

15. The method according to claim 2, wherein said antipsychotic drug is haloperidol.

16. A method for preventing a decrease in dopamine levels in nigrostriatal axon terminals in the striatum of a mammal, said decrease associated with the development of tardive dyskinesia associated with neuroleptic treatment of schizophrenia, comprising:

a) providing:
   i) a $D_2$ receptor-blocking neuroleptic drug; and
   ii) taurine or a similarly acting analogue; and
b) co-administering during a course of treatment a combination of a therapeutically effective amount of said neuroleptic drug and a therapeutically effective amount of taurine or said analogue over a period of time sufficient for said combination to prevent a statistically significant decrease in striatal dopamine levels.

17. The method according to claim 16, wherein said neuroleptic is selected from the group consisting of chlorpromazine, haloperidol, thioridazine, mesoridazine, piperacetazine, trifluoperazine, perphenazine, fluphenazine, thiothixene, loxapine, molindone, and any drug known as a major tranquilizer, neuroleptic, or antipsychotic.

18. The method according to claim 17, wherein said neuroleptic is haloperidol.

19. A method for preventing an elevation in the numbers of dopamine receptors in a mammal following chronic administration of $D_2$ receptor-blocking anti-psychotic drugs, said elevation associated with the development of tardive dyskinesia, comprising:

a) providing:
   i) a $D_2$ receptor-blocking anti-psychotic drug; and
   ii) taurine or a similarly acting analogue; and
b) co-administering a combination of a therapeutically effective amount of said drug and a therapeutically effective amount of taurine or said analogue over a period of time sufficient for said combination to prevent a statistically elevation in the number of dopamine receptors.

20. The method according to claim 19, wherein said neuroleptic is selected from the group consisting of chlorpromazine, haloperidol, thioridazine, mesoridazine, piperacetazine, trifluoperazine, perphenazine, fluphenazine, thiothixene, loxapine, molindone, and any drug known as a major tranquilizer, neuroleptic, or antipsychotic.

21. The method according to claim 20, wherein said neuroleptic is haloperidol.

22. The method according to claim 19, wherein said analogue of taurine is selected from the group consisting of 5 β-taurocholenic acids, 5 β-taurocholadienic acids, L-gamma-glutamyl taurine, taurine-containing peptides of the formula:

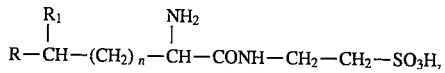

taurinamide, phthalyltaurine, sulfonamide derivatives of taurine, taurine derivatives represented by the general formula: $(CH_3-CO-NH-CH_2-CH_2-SO_3)_n-M^+$, where M is an alkali metal or an alkaline earth metal of valence n, wherein n=1 or 2 and N-acetyl-L-aspartyltaurine.

23. A method for preventing striatal excitotoxicity leading to the development of tardive dyskinesia, comprising administering a therapeutically effective amount of a $D_2$ receptor-blocking neuroleptic drug in combination with a therapeutically effective amount of taurine or a taurine derivative, wherein taurine or said derivative interferes with calcium influx at the postsynaptic level following the presynaptic release of glutamate, thereby blocking excitotoxicity.

24. The method according to claim 23, wherein said neuroleptic is selected from the group consisting of chlorpromazine, haloperidol, thioridazine, mesoridazine, piperacetazine, trifluoperazine, perphenazine, fluphenazine, thiothixene, loxapine, molindone, and any drug known as a major tranquilizer, neuroleptic, or antipsychotic.

25. The method according to claim 24, wherein said neuroleptic is haloperidol.

26. The method according to claim 23, wherein said analogue of taurine is selected from the group consisting of 5 β-taurocholenic acids, 5 β-taurocholadienic acids, L-gamma-glutamyl taurine, taurine-containing peptides of the formula:

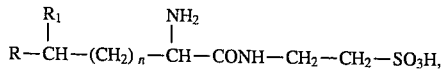

taurinamide, phthalyltaurine, sulfonamide derivatives of taurine, taurine derivatives represented by the general formula: $(CH_3-CO-NH-CH_2-CH_2-SO_3)_n-M^+$, where M is an alkali metal or an alkaline earth metal of valence n, wherein n=1 or 2 and N-acetyl-L-aspartyltaurine.

27. A method for preventing striatal excitotoxicity leading to the development of tardive dyskinesia, comprising administering a therapeutically effective amount of a $D_2$ receptor-blocking neuroleptic drug in combination with a nitric oxide synthase inhibitor, wherein said synthase inhibitor prevents the conversion of arginine to nitric oxide, thereby blocking excitotoxicity.

28. The method according to claim 27, wherein said neuroleptic is selected from the group consisting of chlorpromazine, haloperidol, thioridazine, mesoridazine, piperacetazine, trifluoperazine, perphenazine, fluphenazine, thiothixene, loxapine, molindone, and any drug known as a major tranquilizer, neuroleptic, or antipsychotic.

29. The method according to claim 28, wherein said neuroleptic is haloperidol.

30. The method according to claim 27, wherein said synthase inhibitor is methyl arginine or nitroarginine.

31. The method according to claim 1, claim 12, claim 16, claim 19, claim 23, or claim 27 wherein said drug is administered in an amount of from about 0.1 to about 2000 mg/kg of body weight daily, and taurine is co-administered with said drug in an amount of from about 0.1 to about 2500 mg/kg of body weight daily.

32. The method according to claim 31, wherein said drug is administered in an amount of from about 1 to about 1000 mg/kg of body weight daily and taurine, or analogues thereof, is co-administered with said drug in an amount of from about 0.5 to about 250 mg/kg of body weight daily.

33. The method according to claim 32, wherein said drug is administered in an amount of from about 10 to about 500 mg/kg of body weight daily and taurine, or analogues thereof, is co-administered with said drug in an amount of from about 5 to about 150 mg/kg of body weight daily.

34. The method according to claim 14, 22, or 26, wherein said alkali metal is $K^+$ or $Li^{++}$, and wherein said alkaline earth metal of valence n=1 or 2 is $Ca^{++}$, $Mg^{++}$ or $Mn^{++}$.

* * * * *